(12) United States Patent
Borgmeier et al.

(10) Patent No.: US 10,433,898 B2
(45) Date of Patent: *Oct. 8, 2019

(54) TAPERED PRECISION BLADE ELECTROSURGICAL INSTRUMENT

(71) Applicant: Megadyne Medical Products, Inc., Draper, UT (US)

(72) Inventors: Paul R. Borgmeier, Salt Lake City, UT (US); Brian J. Walter, South Jordan, UT (US); Darcy W. Greep, Herriman, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 387 days.

This patent is subject to a terminal disclaimer.

(21) Appl. No.: 14/994,692

(22) Filed: Jan. 13, 2016

(65) Prior Publication Data

US 2016/0199118 A1 Jul. 14, 2016

Related U.S. Application Data

(60) Provisional application No. 62/102,736, filed on Jan. 13, 2015.

(51) Int. Cl.
*A61B 18/14* (2006.01)
*A61B 18/00* (2006.01)

(52) U.S. Cl.
CPC .......... *A61B 18/14* (2013.01); *A61B 18/1402* (2013.01); *A61B 2018/00601* (2013.01); *A61B 2018/1412* (2013.01)

(58) Field of Classification Search
CPC ........ A61B 2018/1412; A61B 18/1402; A61B 18/14; A61B 2018/00136; A61B 2018/00601

See application file for complete search history.

(56) References Cited

U.S. PATENT DOCUMENTS 3,911,241 A 10/1975 Jarrard
4,202,337 A 5/1980 Hren
(Continued)

FOREIGN PATENT DOCUMENTS

KR 20010006154 11/2001
KR 20020066000 8/2002
(Continued)

OTHER PUBLICATIONS

International Search Report and Written Opinion for PCT/US2015/011127, dated May 6, 2015.
U.S. Appl. No. 14/994,678, filed Jan. 13, 2016.

*Primary Examiner* — Jaymi E Della
*Assistant Examiner* — Sean W Collins
(74) *Attorney, Agent, or Firm* — Workman Nydegger

(57) ABSTRACT

An electrosurgical electrode comprises an elongated body having a cross-sectional area and longitudinal side edges forming longitudinal cutting edges adapted for electrosurgical dissection along a plane. The body has a configuration, wherein: the thickness of the side edge is less than or equal to 0.01", forming only one cutting edge, and the cross-sectional area-to-number of cutting edges ratio is less than or equal to 0.000150 in$^2$ per cutting edge; or the thickness of a first side edge is greater than 0.01" and the thickness of a second side edge is less than or equal to 0.01", and the cross-sectional area-to-number of cutting edges ratio is less than or equal to 0.001 in$^2$ per cutting edge.

24 Claims, 8 Drawing Sheets

(56) References Cited

U.S. PATENT DOCUMENTS

| | | | |
|---|---|---|---|
| 4,228,800 A | 10/1980 | Degler | |
| 4,657,016 A | 4/1987 | Garito et al. | |
| 4,765,331 A | 8/1988 | Petruzzi et al. | |
| 4,924,882 A | 5/1990 | Donovan | |
| 5,080,660 A | 1/1992 | Buelna | |
| 5,100,402 A | 3/1992 | Peter | |
| 5,505,728 A | 4/1996 | Ellman et al. | |
| 5,556,397 A | 9/1996 | Long et al. | |
| 5,833,689 A | 11/1998 | Long | |
| 5,860,976 A | 1/1999 | Billings et al. | |
| 5,919,189 A | 7/1999 | Benderev | |
| 5,925,040 A | 7/1999 | Nardella et al. | |
| 5,957,921 A | 9/1999 | Mirhashemi et al. | |
| 6,030,383 A | 2/2000 | Benderev | |
| 6,039,735 A | 3/2000 | Greep | |
| 6,066,137 A | 5/2000 | Greep | |
| 6,126,656 A | 10/2000 | Billings | |
| 6,287,305 B1 | 9/2001 | Heim et al. | |
| 6,533,781 B2 * | 3/2003 | Heim | A61B 18/14 606/45 |
| 6,572,613 B1 | 6/2003 | Ellman | |
| 6,620,160 B2 | 9/2003 | Lewis et al. | |
| 6,749,603 B2 | 6/2004 | Dubnack et al. | |
| 6,780,178 B2 | 8/2004 | Palankar et al. | |
| 6,896,675 B2 | 5/2005 | Leung et al. | |
| 6,960,209 B2 | 11/2005 | Clague et al. | |
| 6,979,328 B2 | 12/2005 | Baerveldt et al. | |
| 7,125,406 B2 | 10/2006 | Given | |
| 7,238,185 B2 | 7/2007 | Palankar et al. | |
| 7,294,127 B2 | 11/2007 | Leung et al. | |
| 7,357,802 B2 | 4/2008 | Palankar et al. | |
| 7,377,919 B2 | 5/2008 | Heim et al. | |
| 7,468,042 B2 | 12/2008 | Turovskiy et al. | |
| 7,527,624 B2 | 5/2009 | Dubnack et al. | |
| 7,537,594 B2 | 5/2009 | Sartor | |
| 7,736,361 B2 | 6/2010 | Planker | |
| 7,785,321 B2 | 8/2010 | Baerveldt et al. | |
| 7,789,879 B2 | 9/2010 | Palankar et al. | |
| 7,846,108 B2 | 12/2010 | Turovskiy et al. | |
| 7,867,225 B2 | 1/2011 | Heim | |
| 7,867,226 B2 | 1/2011 | Heim | |
| 7,922,713 B2 | 4/2011 | Geisel | |
| 7,935,112 B2 | 5/2011 | Heim et al. | |
| 7,935,113 B2 | 5/2011 | Heim et al. | |
| 8,043,286 B2 | 10/2011 | Palankar et al. | |
| 8,177,783 B2 | 5/2012 | Davison et al. | |
| 8,323,276 B2 | 12/2012 | Palanker et al. | |
| 8,382,748 B2 | 2/2013 | Geisel | |
| 8,414,572 B2 | 4/2013 | Davison et al. | |
| 8,439,910 B2 | 5/2013 | Greep et al. | |
| 8,512,321 B2 | 8/2013 | Baerveldt et al. | |
| 8,518,036 B2 | 8/2013 | Leung et al. | |
| 8,562,603 B2 | 10/2013 | Heim et al. | |
| 8,632,537 B2 | 1/2014 | McNall | |
| 8,740,897 B2 | 6/2014 | Leung | |
| 2002/0111608 A1 | 1/2002 | Baerveldt et al. | |
| 2003/0078573 A1 | 4/2003 | Truckai et al. | |
| 2003/0208200 A1 | 11/2003 | Palankar et al. | |
| 2004/0049183 A1 | 3/2004 | Ellman et al. | |
| 2004/0054370 A1 | 3/2004 | Given | |
| 2004/0199157 A1 | 4/2004 | Palankar et al. | |
| 2005/0177211 A1 | 4/2005 | Leung et al. | |
| 2006/0106370 A1 | 5/2006 | Baerveldt et al. | |
| 2006/0111706 A1 | 5/2006 | Truckai et al. | |
| 2006/0241588 A1 * | 10/2006 | Heim | A61B 18/1402 606/48 |
| 2007/0038212 A1 | 2/2007 | Given | |
| 2007/0239156 A1 | 3/2007 | Palankar et al. | |
| 2007/0093811 A1 | 4/2007 | Nesbitt | |
| 2007/0156137 A1 | 7/2007 | Geisel | |
| 2008/0119841 A1 | 1/2008 | Geisel | |
| 2008/0039832 A1 | 2/2008 | Palankar et al. | |
| 2008/0065062 A1 | 3/2008 | Leung et al. | |
| 2008/0140066 A1 | 6/2008 | Davison et al. | |
| 2009/0069802 A1 | 3/2009 | Garito et al. | |
| 2010/0174283 A1 | 7/2010 | McNall, III et al. | |
| 2011/0077626 A1 | 3/2011 | Baerveldt et al. | |
| 2011/0184410 A1 | 7/2011 | Greep et al. | |
| 2012/0053583 A1 | 3/2012 | Palankar et al. | |
| 2012/0083680 A1 | 4/2012 | Carr | |
| 2012/0143186 A1 | 6/2012 | McNall, III et al. | |
| 2012/0330311 A1 | 6/2012 | McNall, III et al. | |
| 2012/0203219 A1 | 8/2012 | Evans et al. | |
| 2012/0215217 A1 | 8/2012 | Horner | |
| 2013/0197506 A1 | 3/2013 | Evans et al. | |
| 2013/0289545 A1 | 3/2013 | Baerveldt et al. | |
| 2013/0110108 A1 | 5/2013 | Davison et al. | |
| 2014/0025060 A1 | 1/2014 | Kerr | |
| 2014/0100557 A1 | 4/2014 | Bohner et al. | |
| 2014/0135757 A1 | 5/2014 | Bernard | |
| 2014/0276849 A1 * | 9/2014 | Voic | A61B 17/320068 606/83 |

FOREIGN PATENT DOCUMENTS

| | | |
|---|---|---|
| WO | 1999040858 | 8/1999 |
| WO | 2000016706 | 3/2000 |

* cited by examiner

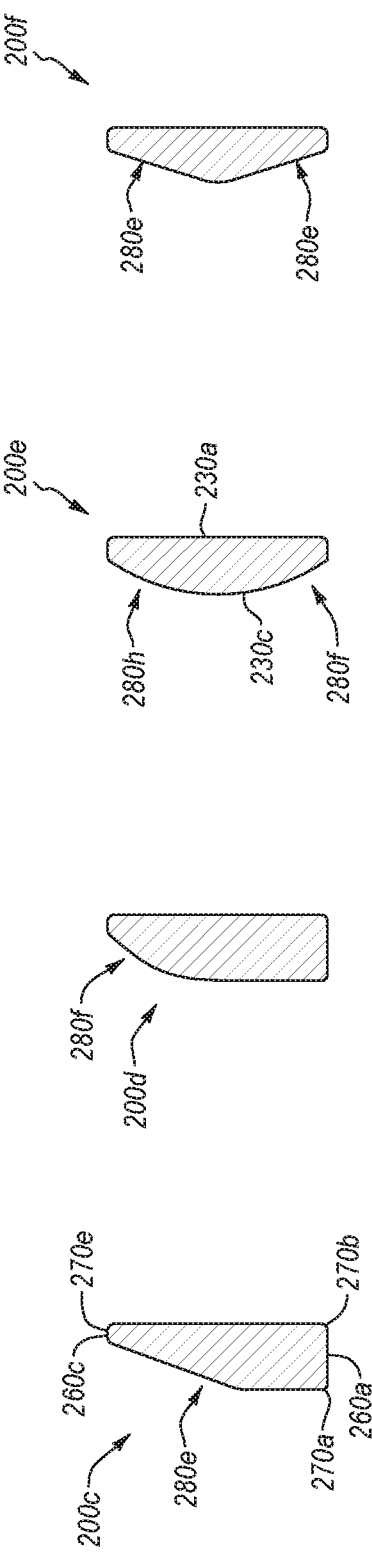

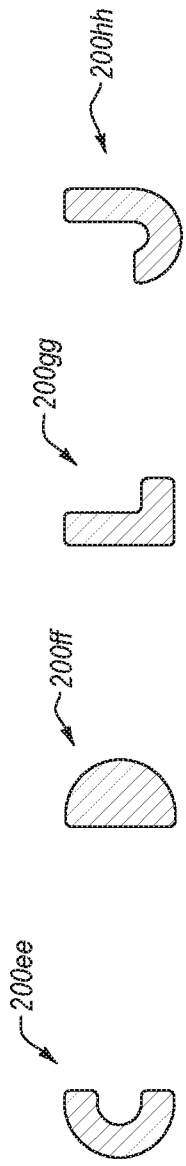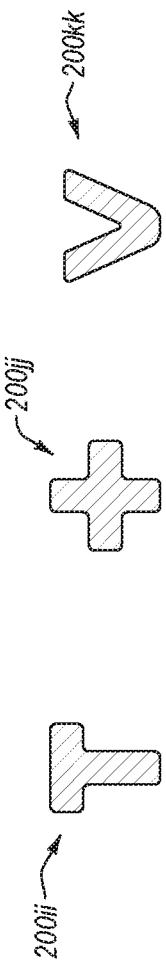

TAPERED PRECISION BLADE ELECTROSURGICAL INSTRUMENT

CROSS-REFERENCE TO RELATED APPLICATIONS

This application claims priority to and the benefit of U.S. Provisional Patent Application Ser. No. 62/102,736, filed Jan. 13, 2015, entitled "Tapered Precision Blade Electrosurgical Instrument," the disclosure of which is incorporated herein by this reference.

BACKGROUND

1. Technical Field

This disclosure relates to electrosurgical devices. More particularly, the disclosure relates to electrosurgical electrodes for use in performing electrosurgery.

2. The Relevant Technology

Modern surgical techniques frequently involve cutting tissue and/or and cauterizing cut tissue to coagulate or stop bleeding encountered during performance of a surgical procedure. In the area of electrosurgery, medical procedures of cutting tissue and/or cauterizing leaking blood vessels are performed by utilizing radio frequency (RF) electrical energy. The RF energy is produced by a wave generator and transmitted to a patient's tissue through a hand-held electrode that is operated by a surgeon. The hand-held electrode delivers an electrical discharge to cellular matter of the patient's body adjacent to the electrode. The discharge causes the cellular matter to heat up in order to cut tissue and/or cauterize blood vessels. For a historical perspective and details of such techniques, reference is made to U.S. Pat. No. 4,936,842, issued to D'Amelio et al., and entitled "Electroprobe Apparatus," the entire disclosure of which is incorporated herein by this reference.

Electrosurgery is widely used and offers many advantages including the use of a single surgical instrument for both cutting and cauterizing/coagulating. Typical monopolar electrosurgical systems have an active electrode, such as in the form of an electrosurgical instrument having a hand piece and a conductive electrode (e.g., tip or blade), which is applied by the surgeon to the patient at the surgical site to perform surgery, and a return electrode to connect the patient back to the generator, thus completing the circuit. The electrode of the electrosurgical instrument produces a high density RF current at the point of contact with the patient in order to produce a surgical effect of cutting or coagulating the tissue. The return electrode carries the same RF current provided to the electrode or tip of the electrosurgical instrument, after the RF current passes through the patient, by completing the circuit, thus providing a path back to the electrosurgical generator.

A variety of proposals have heretofore been embodied in existing electrosurgical implements. Examples of such proposals include those set forth in: U.S. Pat. No. 4,534,347 to Leonard S. Taylor; U.S. Pat. No. 4,674,498 to Peter Stasz; and U.S. Pat. No. 4,785,807 to G. Marsden Blanch, the entire disclosure of each of which is incorporated herein by this reference. The former two of the foregoing patents illustrate implements having sharpened exposed edges (e.g., knife-blade like geometries) which are employed to perform conventional mechanical cutting of tissue. The latter of the patents sets forth an unsharpened blade which has been entirely coated with an insulating layer so that cutting is performed by electrical energy capacitively transferred across the insulating layer rather than by conventional mechanical action.

It is widely accepted that in electrosurgery, "cutting" is accomplished when energy transfer is sufficient to cause water in tissue cells to boil, thus rupturing the cell membranes by internal rather than external forces. A high level of energy is required to effectuate such electrosurgical cutting, leading to a corresponding high temperature of the electrode. The high temperatures involved in electrosurgery can cause thermal necrosis of the tissue adjacent the electrode. The longer tissue is exposed to the high temperatures involved with electrosurgery, the more likely it is that the tissue will suffer thermal necrosis. Thermal necrosis of the tissue can decrease the speed of cutting the tissue and increase post-operative complications, eschar production, and healing time, as well as increasing incidences of heat damage to tissue away from the cutting site.

While the Blanch proposals have constituted an important advance in the art and have found wide-spread acceptance in the field of electrosurgery, there has been a continuing need for further improvement in electrosurgery to increase the precision of cutting and reduce thermal necrosis, thereby decreasing healing time and post-operative complication, reducing eschar production, reducing incidence of heat damage to tissue away from the cutting site, and increasing the speed of cutting. In particular, traditional electrosurgical electrodes are not very precise in their application of energy and as a result, the thermal spread and tissue damage they create can be problematic. Likewise, traditional electrodes are not effectively maneuverable in small, compact, or sensitive tissue locations. For this reason, traditional monopolar electrosurgical electrodes have not been highly effective in certain procedures or under certain conditions (e.g., neurological/spinal/cranial surgeries and pediatric procedures).

To overcome these and other disadvantages in the use of traditional electrosurgical electrodes for electrosurgery, electrosurgical needle electrodes have been employed with some degree of success. However, electrosurgical needles have certain limitations, especially in their dissection or cutting capabilities (e.g., long incisions or dissections along a plane) and maneuverability.

Accordingly, there are a number of disadvantages in conventional electrosurgical devices that can be addressed. Specifically, it would be advantageous to have an electrode that is highly maneuverable and adapted for dissecting or cutting along a tissue plane, and that limits unwanted tissue damage, reduces post-operative complications, increases the speed and precision of cutting, and facilitates quicker healing. The subject matter disclosed and/or claimed herein, however, is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to precision electrosurgical electrodes or blades that are highly maneuverable and adapted for dissecting or cutting along a tissue plane. In addition, the precision electrosurgical electrodes or blades can limit unwanted tissue damage, reduce post-operative complications, increase the speed and precision of cutting, and/or facilitate quicker healing. For instance, an embodiment includes an electrosurgical electrode adapted for use in performing electrosurgical operative procedures. The electrode can comprise a body extending between a first end and a second end. The body can be formed of a conductive material and may be electrically connected to an electrosurgical generator (e.g., to facilitate communication of electrical energy from the generator to the body of the electrode and/or for communicating radio frequency electrical energy to patient tissue for performing an electrosurgical operative procedure thereupon).

In at least one embodiment, the body can comprise: (i) one or more major surfaces (e.g., a first major surface and a second major surface opposite the first major surface); (ii) one or more longitudinal side edges (e.g., disposed at least partially between the first major surface and the second major surface and/or extending a length from the first end towards the second end); and/or (iii) a cross-sectional area (e.g., disposed at least partially between the first major surface and/or the second major surface and/or the one or more longitudinal side edges).

In one or more embodiments, at least one of the longitudinal side edges has a thickness (e.g., between the first major surface and the second major surface). Furthermore, the longitudinal side edges can be adapted for electrosurgically dissecting the tissue along a plane extending from a first location of the tissue to a second location of the tissue, the second location being separated from the first location by a distance in a direction generally perpendicular to the longitudinal side edge.

In at least one embodiment, the thickness of the longitudinal side edge(s) can be greater than about 0.01 inches (0.254 mm). When a longitudinal side edge has a thickness greater than about 0.01 inches, the longitudinal side edge can form or include two or more longitudinal cutting edges, and/or the body can comprise a cross-sectional area-to-number of longitudinal cutting edges ratio that is less than or equal to about 0.0004 square inches per longitudinal cutting edge ($in^2/E$).

In one or more other embodiments, the longitudinal side edge(s) can have a thickness that is less than or equal to about 0.01 inches. When a longitudinal side edge has a thickness less than or equal to about 0.01 inches, the longitudinal side edge can form or include one longitudinal cutting edge, and/or the body can comprise a cross-sectional area-to-number of longitudinal cutting edges ratio that is less than or equal to about 0.000150 square inches per longitudinal cutting edge ($in^2/E$).

In one or more other embodiments, an electrode can include one or more longitudinal side edges that have a thickness that is less than or equal to about 0.01 inches (each comprising one longitudinal cutting edge) and one or more longitudinal side edges that have a thickness that is greater than about 0.01 inches (each comprising two or more longitudinal cutting edges). When an embodiment includes a hybrid of longitudinal side edge(s) having thickness(es) less than or equal to about 0.01 inches and longitudinal side edge(s) having thickness(es) greater than about 0.01 inches, the body of the electrode can comprise a cross-sectional area-to-number of longitudinal cutting edges ratio that is less than or equal to about 0.001 square inches per longitudinal cutting edge ($in^2/E$).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of exemplary embodiments of the present disclosure will be set forth in the description which follows, and in part will be apparent from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 5A-5H each illustrate a cross-sectional view of an exemplary electrosurgical electrode according to an embodiment of the present disclosure;

FIGS. 8A-8G each illustrate a cross-sectional view of an exemplary electrosurgical electrode according to an embodiment of the present disclosure.

DETAILED DESCRIPTION

Figure 1:
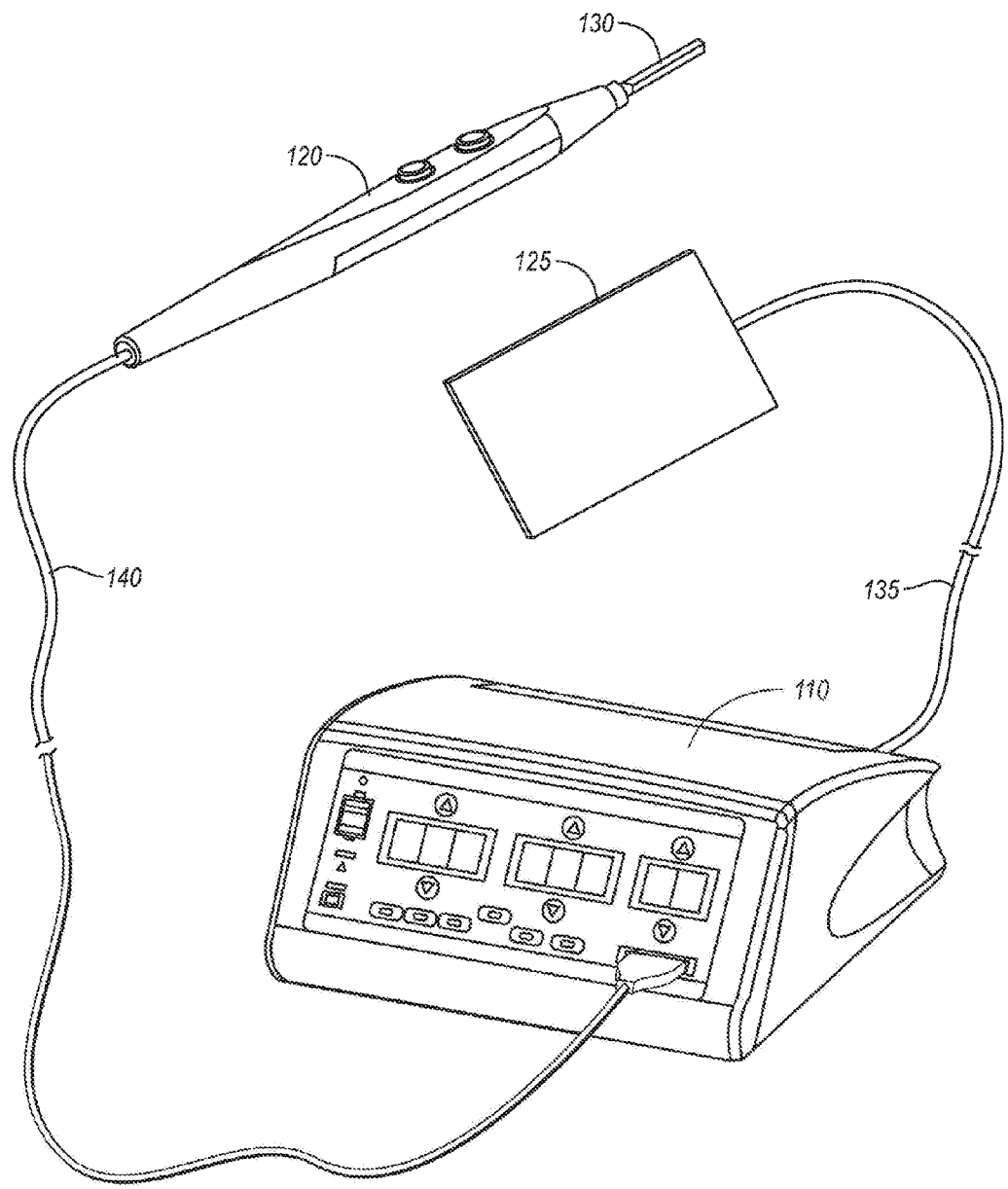
FIG. 1 illustrates a schematic view of an exemplary electrosurgical system according to an embodiment of the present disclosure.

Before describing the present disclosure in detail, it is to be understood that this disclosure is not limited to parameters of the particularly exemplified systems, methods, apparatus, products, processes, compositions, and/or kits, which may, of course, vary. It is also to be understood that the terminology used herein is only for the purpose of describing particular embodiments of the present invention, and is not intended to limit the scope of the invention in any manner. Thus, while the present disclosure will be described in detail with reference to specific configurations, the descriptions are illustrative and are not to be construed as limiting the scope of the present invention. Various modifications can be made to the illustrated configurations without departing from the spirit and scope of the invention as defined by the claims. For better understanding, like components have been designated by like reference numbers throughout the various accompanying figures.

The present disclosure relates to precision electrosurgical electrodes or blades that are highly maneuverable and adapted for dissecting or cutting along a tissue plane. In addition, the precision electrosurgical electrodes or blades can limit unwanted tissue damage, reduce post-operative complications, increase the speed and precision of cutting, and/or facilitate quicker healing. For instance, an embodiment includes an electrosurgical electrode adapted for use in performing electrosurgical operative procedures. The electrode can comprise a body extending between a first end and a second end. The body can be formed of a conductive material and may be electrically connected to an electrosurgical generator (e.g., to facilitate communication of electrical energy from the generator to the body of the electrode and/or for communicating radio frequency electrical energy to patient tissue for performing an electrosurgical operative procedure thereupon).

In at least one embodiment, the body can comprise: (i) one or more major surfaces (e.g., a first major surface and a second major surface opposite the first major surface); (ii) one or more longitudinal side edges (e.g., disposed at least partially between the first major surface and the second major surface and/or extending a length from the first end towards the second end); and/or (iii) a cross-sectional area (e.g., disposed at least partially between the first major surface and/or the second major surface and/or the one or more longitudinal side edges).

In one or more embodiments, at least one of the longitudinal side edges has a thickness (e.g., between the first major surface and the second major surface). Furthermore, the longitudinal side edges can be adapted for electrosurgically dissecting the tissue along a plane extending from a first location of the tissue to a second location of the tissue, the second location being separated from the first location by a distance in a direction generally perpendicular to the longitudinal side edge.

In at least one embodiment, the thickness of the longitudinal side edge(s) can be greater than about 0.01 inches (0.254 mm). When a longitudinal side edge has a thickness greater than about 0.01 inches, the longitudinal side edge can form or include two or more longitudinal cutting edges, and/or the body can comprise a cross-sectional area-to-number of longitudinal cutting edges ratio that is less than or equal to about 0.0004 square inches per longitudinal cutting edge (in2/E).

In one or more other embodiments, the longitudinal side edge(s) can have a thickness that is less than or equal to about 0.01 inches. When a longitudinal side edge has a thickness less than or equal to about 0.01 inches, the longitudinal side edge can form or include one longitudinal cutting edge, and/or the body can comprise a cross-sectional area-to-number of longitudinal cutting edges ratio that is less than or equal to about 0.000150 square inches per longitudinal cutting edge.

In one or more other embodiments, an electrode can include one or more longitudinal side edges that have a thickness that is less than or equal to about 0.01 inches (each comprising one longitudinal cutting edge) and one or more longitudinal side edges that have a thickness that is greater than about 0.01 inches (each comprising two or more longitudinal cutting edges). When an embodiment includes a hybrid of longitudinal side edge(s) having thickness(es) less than or equal to about 0.01 inches and longitudinal side edge(s) having thickness(es) greater than about 0.01 inches, the body of the electrode can comprise a cross-sectional area-to-number of longitudinal cutting edges ratio that is less than or equal to about 0.001 square inches per longitudinal cutting edge (in$^2$/E).

As used herein, "side edge," "longitudinal side edge," and similar terms refer to a transition area and/or structural feature between two major surfaces. Those skilled in the art will appreciate that even a continuous surface that wraps around from an arbitrary starting point back to said starting point can form two major surfaces (e.g., one on either side of the starting point). Similarly, a continuous surface that wraps around to bring one end thereof into proximity with another (opposing) end can form two major surfaces As used herein, "cutting edge," "longitudinal cutting edge," and similar terms refer to a portion of an electrosurgical electrode that is structurally operable, adapted, and/or configured to, and/or capable of, dissecting a patient's tissue in, along, and/or through an anatomical or naturally occurring tissue plane or line of separation between tissue types, tissue borders, or structures. Those skilled in the art will appreciate that such dissection occurs along and/or over a distance (e.g., from a first position toward a second position). Furthermore, the electrosurgical dissection plane can comprise a straight line, curved line, angled line, circular line (where the second position corresponds to the first position after dissection along the distance), and/or combinations thereof.

One or more embodiments implement so called "precision technology," which limits the cross-sectional area of the electrode in combination with at least one or more edges arranged parallel to the longitudinal length of the electrode. In some embodiments, precision technology design principle(s) allows for the creation of electrodes capable of, adapted for, and/or configured for precise application of electrosurgical energy to tissue with enhanced maneuverability, reduced power requirements compared to some existing technologies, low thermal spread that reduces the amount of necrotic damage to the tissue surrounding the incision site compared to some existing technologies, and/or the ability to dissect readily along a plane and/or operate safely within a smaller, narrowed, restricted, constricted or localized area.

The ratio of cross-sectional area (A) to number of longitudinal cutting edges (E), in particular, is unexpectedly important to (or determinant of) one or more benefits of certain embodiments of the present disclosure. Specifically, in one or more embodiments, the body can comprise (only) longitudinal side edge(s) having a thickness greater than about 0.01 inches, at least two longitudinal cutting edges (e.g., associated with each longitudinal side edge), and/or a cross-sectional area-to-number of longitudinal cutting edges ratio that is less than or equal to 0.0004 in$^2$/E. In one or more other embodiments, the body can comprise (only) longitudinal side edge(s) having a thickness less than or equal to about 0.01 inches, one longitudinal cutting edge associated with each longitudinal side edge, and/or a cross-sectional area-to-number of longitudinal cutting edges ratio that is less than or equal to about 0.000150 in$^2$/E. In one or more other embodiments, the body can comprise a hybrid, combination, or mixture of (a) longitudinal side edge(s) having a thickness less than or equal to about 0.01 inches (each having (only) one longitudinal cutting edge associated therewith), and (b) longitudinal side edge(s) having a thickness greater than about 0.01 inches (each having at least two longitudinal cutting edges associated therewith). Hybrid embodiments can have a cross-sectional area-to-number of longitudinal cutting edges ratio that is less than or equal to about 0.001 in²/E. As noted, the measurement of cross-sectional area-to-number of longitudinal cutting edges ratio can be in square inches (in²) per longitudinal cutting edge (E) (i.e., in²/E).

Those skilled in the art will appreciate that the cross-sectional area of embodiments described herein includes the cross-sectional area of the body of the electrosurgical electrode. A variety of cross-sectional area measuring techniques are known in the art and contemplated herein. For instance, the cross-sectional area of a rectangular-shaped body can be determined by measuring and multiplying the (vertical and horizontal) dimensions thereof (e.g., base (or width) times height (or thickness)). Similarly, the cross-sectional area of a triangular-, trapezoidal-, rhomboidal-, and/or diamond-shaped body can be determined by measuring and multiplying the (vertical and horizontal) dimensions thereof and dividing by two (e.g., one-half base (or width) times height (or thickness)).

By way of illustration, if an electrode is constructed with a body having a first side edge thickness less than or equal to 0.01 inches, and a second side edge thickness greater than 0.01 inches, and a uniform, linear tapering between the two edges, the cross-sectional area of the body can be calculated based on the average of these two edge thicknesses (i.e., (first thickness+second thickness)/2). As indicated above, the cross-sectional area to cutting edge ratio for this configuration can be less than or equal to about 0.001 in²/E (i.e., $(W \times T_{ave})/E \leq 0.001$ in²/E).

Without being bound to any theory or restricted to limitations as of the filing of this disclosure, those skilled in the art will also appreciate that manufacturing of electrosurgical electrodes may not allow for the formation of one or more true geometric shapes. In particular, a geometric corner, point, tangent, or intersection of sides, for example, while ideal, may not be attainable by available manufacturing processes or methods. Accordingly, while one or more embodiments described herein may include one or more at least partially rounded edges (e.g., at a microscopic level) those skilled in the art will appreciate that a "rectangular," "triangular," "trapezoidal," or other geometric or non-geometric cross-section may be the most accurate representation or description of the body.

In at least one embodiment, the cross-sectional area can be determined by determining the cross-sectional area of one or more geometric or non-geometric shapes to which the cross-section of the body is closely related (or by which it is most closely approximated). Thus, the cross-sectional area of a substantially rectangular body can be estimated (or determined) by measuring and multiplying the (vertical and horizontal) dimensions thereof (e.g., base (or width) times height). In an alternative embodiment, a true cross-sectional area (e.g., accounting for the absence of small or even minute edge and/or corner roundings) can be determined and/or measured. For instance, modeling software or other measuring mechanisms can be utilized to determine the actual cross-sectional area occupied by the material(s) forming the body of the electrosurgical electrode. Thus, certain embodiments having one or more protrusions or other shaped features can have a true cross-sectional area determined accurately and/or precisely.

In other embodiments, the cross-sectional area can comprise the cross-sectional area circumscribed, encompassed, covered, and/or occupied by the (outer-most) dimensions, edges, protrusions, and/or surfaces of the body (e.g., the least, common dimension(s) and/or cross-sectional area of the body). For instance, the cross-sectional area can comprise the longest or outer-most dimension of the body in the x-plane times the longest or outer-most dimension of the body in the y-plane or other similar calculus.

Certain embodiments may include one or more (concave) channels or grooves in the body of the electrosurgical electrode. Such channels or grooves may appear as a recess in the cross-sectional view of the body. The cross-sectional area of a body having one or more recesses can include both the cross-sectional area of the body portion (or material thereof) and the cross-sectional area of the recess(es) or recessed portion(s). Thus, the cross-sectional area of the body can comprise the cross-sectional area circumscribed by the outer-most dimensions, edges, protrusions, and/or surfaces of the body (e.g., as if the recessed portion(s) we part of the body). In an alternative embodiment, the cross-sectional area of a body having one or more recesses can include only the cross-sectional area of the body portion of the electrode (or physical material thereof).

Similarly, the cross-sectional area of a body having one or more (convex) protrusions can include the cross-sectional area defined and/or circumscribed by the (combined) outer dimensions of the protrusion(s) and the body portion. Thus, any apparently recessed portions between the protrusions can contribute to the cross-sectional area of the body in some embodiments. The cross-sectional area of a body having one or more protrusions can also (or alternatively) comprise the cross-sectional area of the protrusion(s) plus the cross-sectional area of the body portion (without the protrusions). Thus, any apparently recessed portions between the protrusions may not contribute to the cross-sectional area of the body in some embodiments.

In at least one embodiment, a body having one or more concave portions can have a cross-sectional area determined by inclusion of the concave portion in the calculus. For instance, a substantially triangular body having a substantially triangular recessed portion therein (see e.g., FIG. 7N) can have a cross-sectional area that includes the recessed portion as part of the body (i.e., as if there were no concave, recessed portion in the triangular-shaped body). Thus, a body having one or more concave portions can have a cross-sectional area comprising the area circumscribed by the body and one or more concave portions. In other embodiments, a body having no concave portions can have a cross-sectional area equal to the actual cross-sectional area of the material forming the body. Thus, a body having a convex (or entirely convex) body can have a cross-sectional area comprising the area occupied by the body (or suitable approximation thereof, as described above).

As indicated above, embodiments of the present disclosure can include an electrosurgical electrode comprising a body having (i) one or more major surfaces (e.g., a first major surface and a second major surface opposite the first major surface), (ii) one or more longitudinal side edges (e.g., disposed at least partially between the first major surface and the second major surface), at least one of the one or more longitudinal side edges having a thickness greater than about 0.01 inches (0.254 mm), the at least one of the one or more longitudinal side edges having two or more longitudinal cutting edges, (iii) a cross-sectional area (e.g., disposed at least partially between the first major surface and/or the second major surface and/or the one or more longitudinal side edges), and/or (iv) a cross-sectional area-to-number of (effective) longitudinal cutting edge(s) ratio less than or equal to 0.0004 in²/E.

In at least one embodiment, the body can comprise an elongated body extending longitudinally between a first end and a second end. The first and second ends can be separated by a first length. Similarly, the one or more longitudinal side edges can extend a second length between the first end and the second end. In at least one embodiment, the first length and second length can be substantially equal such that one or more longitudinal side edges extend between the first end and the second end. In other embodiments, the second length can be shorter that the first length such that the one or more longitudinal side edges do not extend all the way between the first end and the second end.

In some embodiments, the thickness of the one or more longitudinal side edges and/or the at least one of the one or more longitudinal side edges can be measured between a first major surface and a second major surface (e.g., opposite the first major surface). In some embodiments, the at least one of the one or more longitudinal side edges is continuous with the first major surface and the second major surface such that (i) at least one of the two or more longitudinal cutting edges comprises a junction between the first major surface and the at least one of the one or more longitudinal side edges, and (ii) at least one of the two or more longitudinal cutting edges comprises a junction between the second major surface and the at least one of the one or more longitudinal side edges. Specifically, with a thickness greater than about 0.01 inches, the at least one of the one or more longitudinal side edges can produce and/or present more than one effective longitudinal cutting edge in certain embodiments. Hence, the at least one of the one or more longitudinal side edges has two or more longitudinal cutting edges in some embodiments.

In some embodiments, the one or more longitudinal side edges can comprise a plurality of longitudinal side edges, with at least one of the plurality of longitudinal side edges having two or more longitudinal cutting edges and a thickness greater than about 0.01 inches between the first major surface and the second major surface. Furthermore, the plurality of longitudinal side edges can include at least one longitudinal side edge having a thickness less than or equal to about 0.01 inches between the first major surface and the second major surface. Such hybrid embodiments can have a cross-sectional area-to-number of longitudinal cutting edges ratio that is less than or equal to about 0.001 in$^2$/E.

In another embodiment, the body can comprise (i) one or more major surfaces (e.g., a first major surface and a second major surface opposite the first major surface), (ii) one or more longitudinal side edges (e.g., disposed at least partially between the first major surface and the second major surface), at least one of the one or more longitudinal side edges having a thickness less than or equal to about 0.01 inches (0.254 mm), the at least one of the one or more longitudinal side edges having one longitudinal cutting edge, (iii) a cross-sectional area (e.g., disposed at least partially between the first major surface and/or the second major surface and/or the one or more longitudinal side edges), and/or (iv) a cross-sectional area-to-number of (effective) longitudinal cutting edge(s) ratio less than or equal to about 0.000150 in$^2$/E.

In one or more embodiments, the at least one of the one or more longitudinal side edges is continuous with the first major surface and the second major surface such that the longitudinal cutting edge thereof comprises the junctions between the at least one of the one or more longitudinal side edges and the first and second major surfaces. Specifically, with a longitudinal side edge thickness less than or equal to about 0.01 inches, the at least one of the one or more longitudinal side edges does not produce and/or present more than one effective longitudinal cutting edge in certain embodiments. Hence, the at least one of the one or more longitudinal side edges has one longitudinal cutting edge in some embodiments.

In some embodiments, the cross-sectional area of the body can have a cross-sectional height between the first major surface and the second major surface. The cross-sectional height can be greater than about 0.01 inches. Furthermore, at least one of the one or more major surfaces (e.g., the first major surface and/or the second major surface) can include one or more tapered portions (e.g., extending from a portion of the at least one of the one or more major surfaces to the one or more longitudinal side edges (e.g., the at least one of the one or more longitudinal side edges (having one longitudinal cutting edge)) such that the thickness of the one or more longitudinal side edges is less than or equal to about 0.01 inches). In certain embodiments, the one or more tapered portions can allow the cross-sectional height of the body to be greater than about 0.01 inches and the thickness of the one or more longitudinal side edges to be less than or equal to about 0.01 inches. Thus, a hybrid configuration can be formed by one or more tapered portions. Such hybrid embodiments can have a cross-sectional area-to-number of longitudinal cutting edges ratio that is less than or equal to about 0.001 in$^2$/E.

As indicated above, in some embodiments, the one or more longitudinal side edges can include a plurality of longitudinal side edges (e.g., disposed between the first major surface and the second major surface and extending at least one length between the first end of the body and the second end of the body). At least one of the plurality of longitudinal side edges can have a thickness less than or equal to about 0.01 inches (e.g., between the first major surface and the second major surface).

In some embodiments, the one or more tapered portions can include a plurality of tapered portions (e.g., extending from a portion of at least one of the first major surface and the second major surface to one or more longitudinal cutting edges (e.g., of the plurality of longitudinal cutting edges)). For instance, an embodiment can include a plurality of tapered portions extending from a portion of the first major surface to respective longitudinal side edges of the plurality of longitudinal side edges.

Another embodiment can include one or more tapered portions extending from a portion of the first major surface to one or more of the plurality of longitudinal side edges and one or more tapered portions extending from a portion of the second major surface to one or more of the plurality of longitudinal side edges. Another embodiment can include a plurality of tapered portions extending from a portion of the first major surface to respective longitudinal side edges of the plurality of longitudinal side edges and one or more tapered portions extending from a portion of the second major surface to one or more of the plurality of longitudinal side edges. Another embodiment can include a plurality of tapered portions extending from a portion of the first major surface to respective longitudinal side edges of the plurality of longitudinal side edges and a plurality of tapered portions extending from a portion of the first major surface to respective longitudinal side edges of the plurality of longitudinal side edges.

In certain embodiments, the one or more longitudinal side edges can be continuous with the first major surface and/or the second major surface. Furthermore, the electrode can comprise a tip (e.g., disposed at the first end of the body). The tip can also be disposed at least partially between the first major surface and the second major surface and/or continuous with one or more of the first major surface, the second major surface, and the one or more longitudinal side edges. The tip can also have a blunt configuration, a pointed configuration, a rounded configuration, an angled configuration, or any other suitable configuration.

One or more embodiments can include an insulating coating (e.g., covering at least a portion of the body). The insulating coating can be provided with or at a thickness sufficient to ensure transmission of the radio frequency electrical energy from the body to the tissue. The insulating coating can comprise or be a non-stick coating, as known in the art. The insulating coating can be formed of or comprise a material such as Polyetratluoroethylene (PTFE), silicone, ceramic, glass, fluorinated hydrocarbon, diamond, a high temperature polymer, a hydrophilic polymer, a capacitor dielectric, and/or combinations thereof.

In at least one embodiment, the cross-sectional area of the body can have a cross-sectional width (e.g., between opposing side edges). In one embodiment, the cross-sectional width can be less than or equal to about 0.055 inches. In an alternative embodiment, the cross-sectional width can be greater than about 0.055 inches. The cross-sectional area can also have a cross-sectional height (e.g., between the first major surface and the second major surface). The cross-sectional height can be less than or equal to about 0.01 inches in some embodiments. Alternatively, the cross-sectional height can be greater than about 0.01 inches in some embodiments. Difference(s) between the cross-sectional height and the thickness of one or more side edges can determine and/or contribute to the configuration of the body. For instance, a body having a cross-sectional height less than the thickness of one on or more side edges can have a concave configuration.

Furthermore, the cross-sectional area can have a cross-sectional shape or configuration. For instance, certain embodiments can include one or more rounded, angled, peaked, jagged, smooth, protruding, or other elements, or combinations thereof. For instance, some embodiments can include a (substantially) star cross-section, square cross-section, rectangular cross-section, rhomboid cross-section, parallelogram cross-section, diamond cross-section, airfoil or tear-drop cross-section, partial airfoil or tear-drop cross-section, triangular cross-section, round cross-section with one or more abutments, multi-sided cross-section, arrowhead cross-section, "C"-shaped cross-section, "D"-shaped cross-section, "L"-shaped cross-section, "J"-shaped cross-section, "T"-shaped cross-section, "X"-shaped cross-section, "V"-shaped cross-section, lenticular cross-section, partial lenticular cross-section (e.g., half lenticular, quarter lenticular, etc.), multi-lobe cross-section, semi-circular cross-section, and/or partial "yin-yang" cross-section (e.g., half yin-yang, etc.), including any suitable combination thereof.

One will appreciate that manufacturing restraints may not permit a formation of the perfectly and/or geometrically "pointed" corners required to form one or more of the aforementioned configurations. Regardless, those skilled in the art will appreciate that cross-sectional configurations can comprise at least partially rounded corners and still comprise the cross-sectional shape or configuration recited.

In at least one embodiment, the electrode can be adapted for use in performing electrosurgical operative procedures at a power level that is reduced by at least, about, or greater than 5%, 10%, 15%, 20%, 25%, 30%, 35%, 40%, 45%, 50%, 55%, 60%, 65%, 70%, 75%, 80%, 85%, 90%, 95%, ¼, ⅓, ½, ⅔, ¾ or more than the typical power level used for a standard electrosurgical blade electrode in the same or similar tissue type or location. For example, a typical power level of 30 watts (or J/s) used for general surgical procedures may be reduced to 10 watts when using a precision electrode to accomplish the desired result, with improved thermal outcome and improved user maneuverability. In addition, the electrode can be adapted for a specific use in performing electrosurgical operative procedures at a power level that is reduced by at least, about, or greater than 5%, 10%, 15%, 20%, 25%, 30%, 35%, 40%, 45%, 50%, 55%, 60%, 65%, 70%, 75%, 80%, 85%, 90%, 95%, ¼, ⅓, ½, ⅔, ¾ or more compared to an electrosurgical blade electrode having a cross-section area-to-cutting edge ratio (a) greater about 0.0004 $in^2/E$, (b) greater than about 0.000150 $in^2/E$, and/or (c) greater than about 0.001 $in^2/E$ (e.g., compared to the power level typically used in the same or similar tissue type or location for an electrode with a ratio greater than the above). Thus, embodiments of the present disclosure allow significantly lower power transmission through tissues, thereby making such electrode embodiments readily useful and applicable, especially in sensitive areas or tissues prone to thermal injury, that do not typically benefit from the use of electrosurgery.

Other embodiments include a method of using an electrosurgical electrode (e.g., as described above) for performing an electrosurgical operative procedure. The electrode can be configured according to one or more of the embodiments described herein. In certain embodiments, the method can comprise (i) contacting the tissue with at least one of the one or more longitudinal cutting edges while energizing the electrode with radio-frequency electrical energy communicated from the generator (e.g., at an electrical power level at least ⅔ less than typical electrosurgical settings), thereby severing the tissue, (ii) advancing the energized electrode a certain distance, thereby electrosurgically dissecting the tissue along the plane extending from a first location of the tissue to a second location of the tissue, (iii) removing the at least one of one or more longitudinal cutting edges from contact with the patient tissue, (iv) identifying one or more patient sites needing coagulation, and/or (iv) cauterizing one or more patient sites needing coagulation by contacting the patient site needing coagulation with at least a part of the first major surface or the second major surface and energizing the electrode with radio-frequency electrical energy (e.g., at an electrical power level at least ⅔ less than typical electrosurgical settings) while contacting the one or more patient sites needing coagulation with at least a part of the first major surface or the second major surface, or spray coagulating the tissue from the surfaces and/or edges of the electrode.

In some embodiments, the method can include contacting the tissue with a tip disposed at the first end of the body (e.g., between the first major surface and the second major surface) while energizing the electrode with radio-frequency electrical energy communicated from the generator (e.g., at an electrical power level at least ⅔ less than typical electrosurgical settings), thereby severing the tissue. Furthermore, the method can include advancing the electrode while energizing the electrode with radio-frequency electrical energy communicated from the generator at an electrical power level at least ⅔ less than typical electrosurgical settings, thereby electrosurgically dissecting at least a portion of the tissue along the plane extending from the first location of the tissue to the second location of the tissue.

In at least one embodiment, the electrosurgical operative procedure can include a neurological surgery or procedure, a spinal surgery or procedure, a cranial surgery or procedure, and/or a pediatric surgery or procedure. In certain embodiments, advancing the energized electrode can comprise one or more changes in direction during dissection or while creating an incision. For instance, advancing the energized electrode can comprise a smooth, rounded or sharp, angled change in direction to the right, to the left, upward, or downward (e.g., while advancing the energized electrode along the dissection/incision path or plane).

Turning now to the figures, FIG. 1 and the corresponding discussion are intended to provide a brief, general description of an exemplary electrosurgical system in which one or more embodiments of the present disclosure can be implemented. Specifically, electrosurgical system 100 is illustrated, which includes a wave generator 110, a cable or cord 140, a hand-held instrument or hand piece 120, an electrosurgical electrode 130, a return electrode 125, and a cable or cord 135. Generator 110, in a preferred embodiment, is an RF wave generator. Accordingly, a surgeon or other user can use electrosurgical system 100 during surgical or other procedures to cut patient tissue and/or cauterize blood vessels of the patient's tissue.

In an illustrative electrosurgical procedure, RF electrical energy is produced by a wave generator, such as wave generator 110. The RF electrical energy is transferred to electrode 130 via hand piece 120, which is electrically coupled to wave generator 110 via cord 140. Those skilled in the art will appreciate that wave generator 110 can include a high-frequency oscillator and amplifier(s) to generate an RF electrical energy wave that can be used to cut tissue and/or cauterize blood vessels during electrosurgery.

The RF electrical energy wave powers hand piece 120 in order to produce an electrical discharge from electrode 130 to the patient tissue. The electrical discharge can cause heating of cellular matter of patient tissue that is in direct (or indirect, e.g., close or extremely close) contact with electrode 130. In particular, the energy transfer can be sufficient to cause water in tissue cells to boil, thus rupturing the cell membranes, thereby electrosurgically cutting, severing, and/or dissecting the patient tissue. In at least one embodiment, electrosurgically cutting, severing, and/or dissecting does not involve a significant amount or degree of mechanical cutting, severing, and/or dissecting. In some embodiments, electrode 125 provides a return electrical path via cord 135 to wave generator 110 for charge that dissipates into surrounding tissue of the patient's body. One will appreciate that terms such as cutting, severing, and/or dissecting can be used interchangeably herein to reflect various types of surgical tissue separation, etc.

In some embodiments, during electrosurgery, electrical discharge from electrode 130 can be used to independently or concurrently cut and cauterize. For instance, a constant sinusoidal wave supplied by wave generator 110 and transmitted to hand piece 120 can allow electrode 130 to cut through tissue of the patient's body. Alternatively, a dampened wave supplied by wave generator 110 and transmitted to hand piece 120 can allow electrode 130 to cauterize leaking blood vessels. In at least one embodiment, a combination of the constant sinusoidal wave and the damped wave can be supplied by wave generator 110 to hand piece 120 for allowing electrode 130 to concurrently cut and cauterize, thereby minimizing tissue trauma and blood loss during the surgical procedure. For instance, in one or more embodiments, an alternating transmission of constant sinusoidal wave and/or damped wave can be supplied by wave generator 110 to hand piece 120 for allowing electrode 130 to concurrently cut and cauterize, thereby minimizing tissue trauma and blood loss during the surgical procedure.

Figure 2:
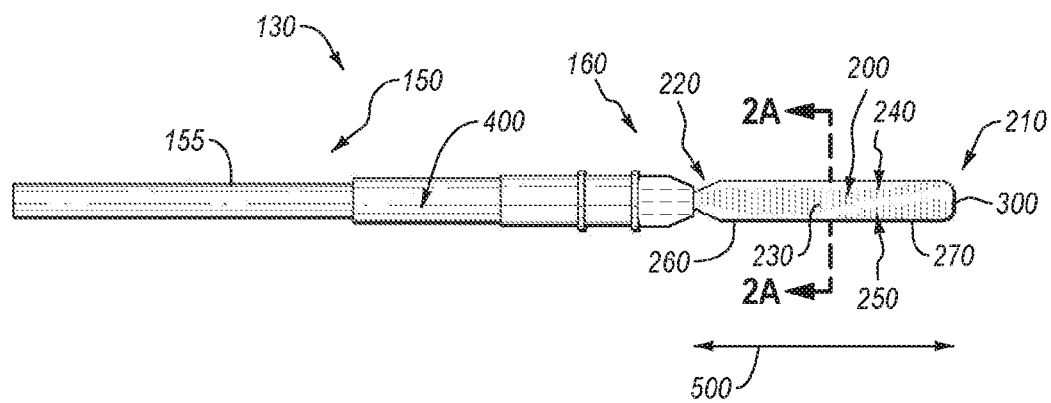
FIG. 2 illustrates a top plan view of an exemplary electrosurgical electrode for use with the electrosurgical system of FIG. 1.
Figure 2A:
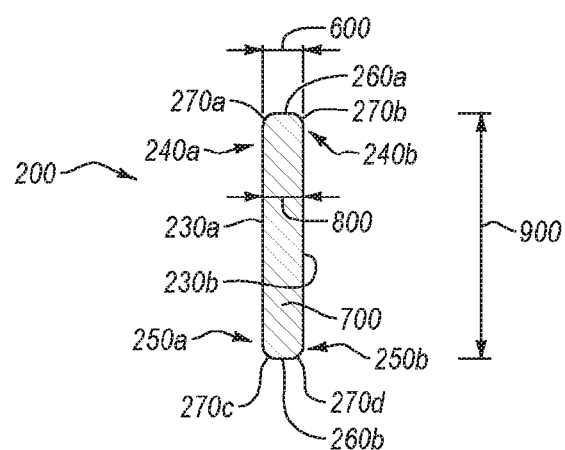
FIG. 2A illustrates a cross-sectional view of the electrosurgical electrode of FIG. 2.
Figure 3:
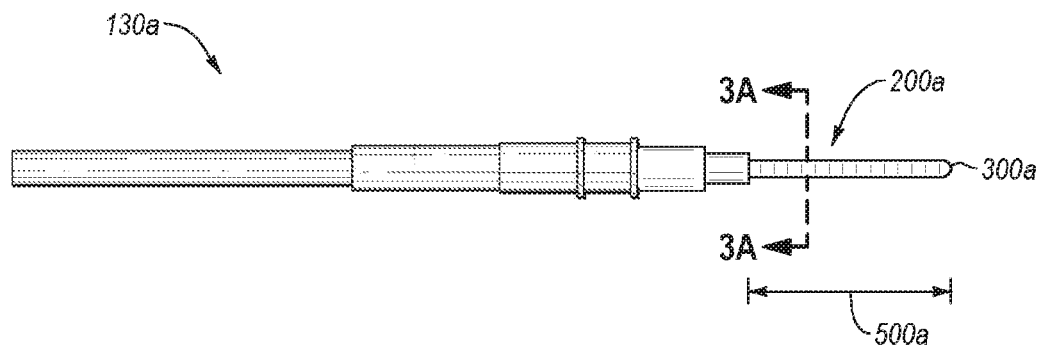
FIG. 3 illustrates a top plan view of another exemplary electrosurgical electrode.
Figure 3A:
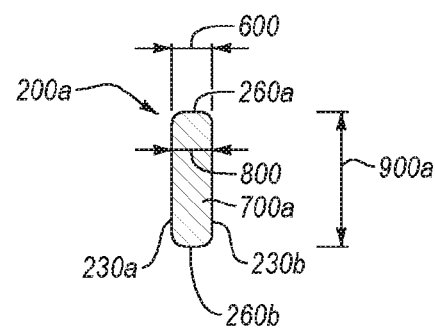
FIG. 3A illustrates a cross-sectional view of the electrosurgical electrode of FIG. 3.
Figure 4:
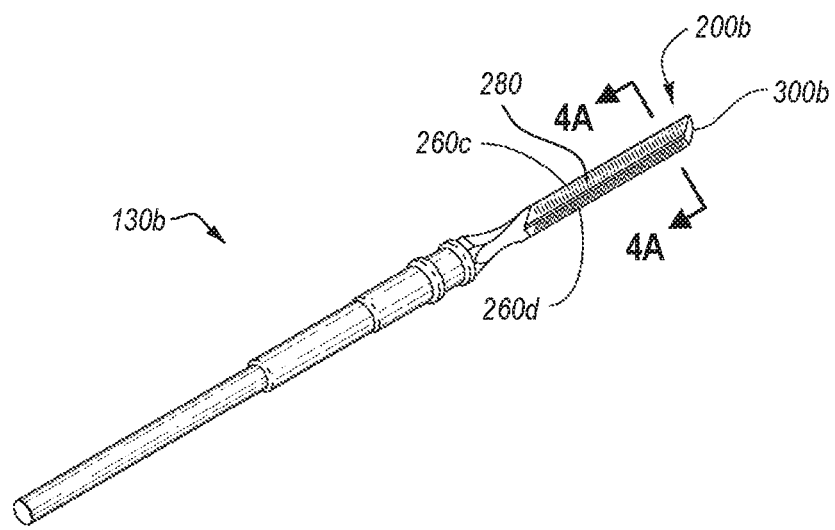
FIG. 4 illustrates a perspective view of another exemplary electrosurgical electrode.

By way of introduction, FIGS. 2, 3, and 4 illustrate an exemplary assortment of (interchangeable) electrodes 130, or various features, designs, and/or configurations thereof. FIGS. 2A, 3A, 4A, and 5A-8G illustrate an exemplary assortment of cross-sectional configurations for (a body of) an electrosurgical electrode 130.

FIG. 2, for example, illustrates a generic electrode for illustrative purposes. As illustrated in FIG. 2, the electrode 130 has (i) a connection end 150 configured to be coupled to a hand piece 120 to allow RF electrical energy generated by wave generator 110 to be transmitted through hand piece 120 to electrode 130, and (ii) a working end 160 configured to contact patient tissue and apply the electrical discharge to the patient tissue. In at least one embodiment, working end 160 and connection end 150 can comprise opposing ends of electrode 130.

One will appreciate, however, that electrode 130 need not comprise an elongated configuration as illustrated in FIG. 2. For instance, electrode 130 can have a curved, angled, circular, flat, broad, or other configuration without departing from the scope of this disclosure. Indeed, in some embodiments, electrode 130 can have any configuration suitable for use in an electrosurgical procedure.

In some embodiments, connection end 150 can include a connection member 155 configured to be coupled to a hand piece 120. The lengths of connection end 150 and/or connection member 155 thereof can vary depending on the specific type of electrode and/or the type of procedure for which the electrode is used. For instance, the lengths of the connection ends may range from about 6.35 cm to about 48 cm in certain embodiments. In various embodiments, the lengths of the connection ends can be about 6.35 cm, 6.9 cm, 10.16 cm, 15.24 cm, 33 cm, 45 cm, and 48 cm, respectively. It will be appreciated that the lengths of the connection ends can be any suitable lengths and are not intended to limit the scope of the present disclosure.

Electrode 130 can also include a sleeve or coating 400 (e.g., that surrounds at least a portion of the electrode 130) to act as an insulator, provide protection, and/or facilitate holding of the electrode 130 by hand piece 120. For example, an insulative material can be applied to a portion of the working end 160 of the electrode 130 in order to provide an insulative barrier between a portion of the working end 160 and a patient tissue.

In one embodiment, the insulative material can be applied around at least a portion of the working end 160 of the electrode 130 (e.g., leaving part (e.g., only a small part) of the electrode tip exposed for use during electrosurgery). For example, the insulative material can cover the entire working end except for about 0.3 cm at an end of the electrode 130 or working end 160 thereof. The exposed portion can then be used to perform electrosurgery without electrical discharge between the rest of the electrode 130 (or working end 160 thereof) and the patient's tissue. In an alternative embodiment, the insulative material can leave a larger portion of the working end 160 of the electrode 130 exposed.

In some embodiments, the coating can comprise PTFE, fluoropolymer, Polyolefin, ceramic, PARYLENE, or combinations thereof. Such coatings can be applied, for example, to a portion of the working end 160 of the electrode 130 in order to provide an insulative barrier between a portion of the working end 160 and a patient's tissue.

The working end 160 of electrode 130 can also include a body 200 configured to contact patient tissue and apply the electrical discharge to the patient's body. Body 200 (and/or other portions of electrode 130) can comprise, include, and/or be formed of a conductive material. For instance, the conductive material can include stainless steel or other non-corrosive materials. Certain embodiments can also or alternatively include, for example, brass, nickel, aluminum, titanium, copper, silver, gold, other types of steel, or alloys (thereof). Some embodiments can also include non-metallic conductive substances (e.g., provided that they possess the inherent qualities of stability and integrity sufficient to meet the desired requisites), such as certain conductive plastics.

As will be discussed in further detail below, the body 200 of electrode 130 can have an elongated design or configuration. For instance, body 200 can include a first end 210 and a second end 220 (e.g., separated by a length identical or similar to length 500). One will appreciate, however, that body 200 need not comprise an elongated configuration as illustrated in FIG. 2. For instance, body 200 can have a curved, angled, circular, flat, broad, or other configuration without departing from the scope of this disclosure. Indeed, in some embodiments, body 200 can have any configuration suitable for use in an electrosurgical procedure.

In at least one embodiment, electrode 130 can optionally include at least one tip 300 (e.g., disposed on, about, and/or adjacent to first end 210 of body 200). For instance, in some embodiments, body 200 can include or comprise tip 300. In certain embodiments, first end 210 can include tip 300 (e.g., tip 300 can extend from first end 210). Similarly, second end 220 can be connected, attached, and/or adjacent to (and/or extend from) connection end 150 or connection member 155 thereof. One will appreciate, however, that designations corresponding to first and/or second are illustrative only and not intended to limit the scope of this disclosure. Thus, in some embodiments, first end 210 can be connected, attached, and/or adjacent to (and/or extend from) connection end 150 or connection member 155 thereof.

Similarly, one or more tips 300 can be disposed at other locations and/or positions about electrode 130, working end 160, and/or body 200. For instance, body 200 can include one or more tips 300 disposed (longitudinally) thereon and/or forming one or more peaks along body 200. As will be discussed in further detail below, tip 300 can have or comprise any configuration, including one or more various design configurations, suitable for one or more particular electrosurgical procedures.

Body 200 can further include at least one major surface 230 and at least one side edge 260. In some embodiments, major surface 230 can include a first side 240 and/or (an opposing) second side 250. In at least one embodiment, side edge(s) 260 can be positioned at or adjacent to first side 240 and/or second side 250 of major surface 230. Furthermore, a longitudinal side edge 260 can extend a length 500 (e.g., between the first end 210 and the second end 220 of an elongated body 200).

In at least one embodiment, side edge 260 can comprise one or more cutting edges 270. For instance, side edge 260 can be continuous with major surface 230 such that cutting edge 270 comprises (or is formed at) the junction between major surface 230 and side edge 260. Similarly, the junction between major surface 230 and side edge 260 can form cutting edge 270.

As illustrated in FIG. 2A, body 200 can include a first major surface 230a (having a first side 240a and second side 250a) and a second major surface 230b (having a first side 240b and second side 250b). First (longitudinal) side edge 260a can be positioned at or adjacent to (or between) first side 240a of first major surface 230a and first side 240b of second major surface 230b. Similarly, second (longitudinal) side edge 260b can be positioned at or adjacent to (or between) second side 250a of first major surface 230a and second side 250b of second major surface 230b.

Furthermore, one or more longitudinal side edge(s) (e.g., longitudinal side edge 260a and/or 260b) can comprise a thickness 600 (e.g., between first major surface 230a and second major surface 230b). For instance, longitudinal side edge 260a can have a thickness 600 between first major surface 230a at or adjacent to first side 240a thereof and second major surface 230b at or adjacent to first side 240b thereof. One will appreciate that longitudinal side edge 260b can be identically, similarly, or differently configured. For instance, longitudinal side edge 260a can have a thickness greater than the thickness of longitudinal side edge 260b, or vice versa.

In at least one embodiment, (the magnitude of) thickness 600 can contribute to and/or determine the number of cutting edges (E) 270 included in body 200. For instance, those skilled in the art will appreciate that in some embodiments once thickness 600 becomes sufficiently large, the transition between first major surface 230a and second major surface 230b (or between a major surface 230 and a side edge 260), comprises, accommodates, forms, and/or permits the formation of two or more cutting edges 270. One will appreciate, however, that side edge 260 can comprise a single cutting edge 270 (e.g., even where thickness 600 is greater than about 0.01 inches) in some embodiments.

In at least one embodiment, a thickness 600 (of side edge 260 and/or between major surfaces 230) greater than about 0.01 inches can comprise, accommodate, form, and/or permit the formation of two or more cutting edges 270. For instance, a thickness 600 of (greater than or equal to) about 0.011, 0.012, 0.0125, 0.015, 0.0175, 0.0185, 0.0195, 0.02, and/or 0.05 inches (or any value or range of values therebetween) can comprise, accommodate, form, and/or permit the formation of two or more (effective) cutting edges 270. Thus, embodiments of the present disclosure can include a thickness of (i) about, (ii) greater than or equal to about, (iii) at least about, and/or (iv) between about 0.011, 0.012, 0.0125, 0.015, 0.0175, 0.0185, 0.0195, 0.02, 0.05, and 0.075 inches (or any value or range of values therebetween).

As illustrated in FIG. 2A, for example, body 200 can comprise four cutting edges 270a, 270b, 270c, and 270d. Specifically, the junction or transition between side edge 260a and first major surface 230a (at first side 240a thereof) can comprise, accommodate, form, and/or permit the formation of a first (distinct and/or effective) cutting edge 270a. Similarly, the junction or transition between side edge 260a and second major surface 230b (at first side 240b thereof) can comprise, accommodate, form, and/or permit the formation of a second (distinct and/or effective) cutting edge 270b. Likewise, the junction or transition between side edge 260b and first major surface 230a (at second side 250a thereof) can comprise, accommodate, form, and/or permit the formation of a third (distinct and/or effective) cutting edge 270c. Similarly, the junction or transition between side edge 260b and second major surface 230b (at second side 250b thereof) can comprise, accommodate, form, and/or permit the formation of a fourth (distinct and/or effective) cutting edge 270d.

As discussed in further detail below, those skilled in the art will also appreciate that once thickness 600 becomes sufficiently small, the transition between first major surface 230a and second major surface 230b, comprises, accommodates, forms, and/or permits the formation of a single cutting edge 270 in some embodiments. For example, as discussed further below, a thickness 600 less than or equal to about 0.01 inches can comprise, accommodate, form, and/or permit the formation of a single cutting edge 270 in some embodiments.

Longitudinal side edges 260a and 260b can also be separated by a width 900. In at least one embodiment, width 900 can comprise the distance between first ends 240a, 240b and second ends 250a, 250b of first and second major surfaces 230a, 230b, respectively. Width 900 can comprise any suitable size, measurement, or value, including those greater than, less than, or equal to the size, measurement, or value of thickness 600 and/or length 500.

Moreover, body 200 can have a cross-sectional area 700 (e.g., disposed between first major surface 230a and second major surface 230b, and between first longitudinal side edge 260a and second longitudinal side edge 260b. One will appreciate, however, that in certain embodiments (e.g., embodiments having a single longitudinal side edge 260 or embodiments having more than two longitudinal side edges 260), cross-sectional area 700 can be differently disposed, bound, defined, and/or configured. Thus, first major surface 230a, second major surface 230b, and one or more longitudinal side edge 260 can at least partially bound a cross-sectional area 700. Cross-sectional area 700 can also have a cross-sectional height 800 (e.g., between first major surface 230a and second major surface 230b).

In some embodiments, the ratio of any of length 500, thickness 600, cross-sectional area 700, cross-sectional height 800, and/or width 900 to any other size, measurement, or value can vary without necessarily departing from the scope of this disclosure. In some embodiments, however, the ratio between two or more of the foregoing sizes, measurements, or values can be important to (or determinant of) one of more benefits of certain embodiments of the present disclosure. For instance, the ratio of cross-sectional area (A) 700 to the number of cutting edges (E) 270, in particular, can be unexpectedly important to one or more of the aforementioned advantages of certain embodiments of the present disclosure.

Turning now to FIGS. 3 and 3A, an electrosurgical electrode 130a can comprise a body 200a. Body 200a (or one or more components thereof) can have a length 500a. As illustrated in FIG. 3A, body 200a can include first and second major surface 230a and 230b (e.g., separated by cross-sectional height 800), and first and second longitudinal side edges 260a and 260b (e.g., each having a thickness 600). In at least one embodiment, body 200a can have a width 900a and/or longitudinal side edges 260a and 260b can be separated by a width 900a. The measurement of width 900a (e.g., along with length 500a, cross-sectional height 800, and/or thickness 600) can contribute to the calculation of cross-sectional area 700a.

In some embodiments, width 900a can be smaller or less than width 900 (see FIG. 2A). A smaller width 900a can permit, allow, and/or enable a higher level of precision in electrosurgical procedures. For instance, a user can limit the production of unwanted tissue damage or injury by reducing width 900 to a width 900a. Specifically, width 900a can allow a user to make a direction change during an electrosurgical procedure without damaging patient tissue to the same degree that would occur with width 900. In at least one embodiment, reduced width 900a can contribute to a reduction in cross-sectional area 700a and/or the size of tip 200a.

In at least one embodiment, thickness 600a (of side edge(s) 260a and/or 260b) can be greater than about 0.01 inches (0.254 mm). In addition, the cross-sectional area 700a-to-number of longitudinal cutting edges 270 ratio can be less than or equal to about 0.0004 square inches per longitudinal cutting edge (in$^2$/E) (e.g., when longitudinal side edge(s) 260 are greater than about 0.01 inches. In an exemplary embodiment, an illustrative body 200a (having a substantially rectangular cross-section) can have a substantially uniform cross-sectional height 800 of about 0.0185 inches (0.4699 mm). Opposing longitudinal side edges 260a and 260b, separated by a width 900a of about 0.05 inches (1.27 mm), can also have thicknesses of about 0.0185 inches (0.4699 mm), respectively. Accordingly, body 200a can have four (4) longitudinal cutting edges 270 and a cross-sectional area 700a of 0.000925 square inches (in$^2$) (0.596773 mm$^2$). As a result, body 200a can have a cross-sectional area 700a-to-number of longitudinal cutting edges 270 ratio of 0.000231 square inches per longitudinal cutting edge (in$^2$/E) (e.g., 0.1492 mm$^2$/E).

One will appreciate that while additional sizes, measurements, values, and/or ratios are contemplated herein, in the foregoing embodiment, each must conform to the required parameters (i.e., a longitudinal side edge thickness greater than about 0.01 inches, and a cross-sectional area 700a-to-number of longitudinal cutting edges 270 ratio that is less than or equal to about 0.0004 in$^2$/E. Thus, any combination of respective sizes, measurements, and/or values (e.g., for a longitudinal side edge thickness greater than about 0.01 inches, longitudinal side edge length, cutting edge length, body length, body width, body height, cross-sectional thickness, cross-sectional width, cross-sectional height, and/or cross-sectional area, etc.) resulting in a cross-sectional area-to-number of longitudinal cutting edges ratio that is less than or equal to about 0.0004 in$^2$/E is contemplated herein.

In one or more other embodiments, the body of the electrosurgical electrode can comprise at least one side edge having a thickness less than or equal to about 0.01 inches, and a cross-sectional area-to-number of longitudinal cutting edges ratio that is less than or equal to about 0.000150 in$^2$/E. In at least one embodiment, a longitudinal side edge having a thickness less than or equal to about 0.01 inches can be achieved by tapering at least a portion of the body from a cross-sectional height of greater than about 0.01 inches to the longitudinal side edge. For instance, referring now to FIGS. 4 and 4A, electrosurgical electrode 130b can have a body 200b having side edges 260c and 260d, a tip 300b, and at least one tapered portion 280.

Figure 4A:
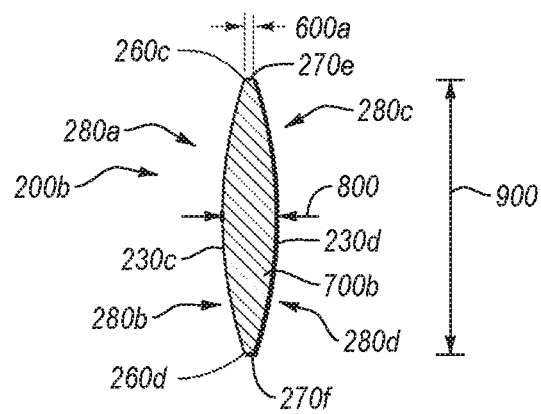
FIG. 4A illustrates a cross-sectional view of the electrosurgical electrode of FIG. 4.

As illustrated in FIG. 4A, body 200b can have opposing major surfaces 230c and 230d, which transition into (or are continuous with) opposing side edges 260c and 260d. Importantly, body 200b can include tapered portion 280a extending from a portion of first major surface 230c to or toward first side edge 260c. Similarly, body 200b can include tapered portion 280b extending from a portion of first major surface 230c to or toward second side edge 260d. Likewise, body 200b can include tapered portion 280c extending from a portion of second major surface 230d to or toward first side edge 260c. Similarly, body 200b can include tapered portion 280d extending from a portion of second major surface 230d to or toward second side edge 260d.

In some embodiments, body 200b can have a height 800 (similar to or different than height 800 of body 200). Likewise, body 200b can have a width 900 (similar to or different than width 900 of body 200). For instance, width 900 can correspond to width 900a in some embodiments. Indeed, the actual (linear or curved) measurement of height 800; width 900, 900a; and/or thickness 600, 600a; can be or comprise any suitable value (e.g., within any range of values or combination of values sufficient to comply with the parameters (for cross-sectional area-to-number of longitudinal cutting edges ratio(s)) disclosed and/or described herein).

Furthermore, because of tapered portions 280, the surface length of major surface 230a and/or 230b from side edge 260c to side edge 260d can be greater or longer than the linear width of body 200b. Similarly, the thickness 600a of side edge(s) 260c, 260d can be less than height 800 of body 200b. Accordingly, the cross-sectional area 700b of body 200b can be less than the product of height 800 and width 900 in some embodiments. Those skilled in the art will also appreciate that reducing height 800 and/or width 900 can decrease cross-sectional area 700b in some embodiments.

Those skilled in the art will appreciate that once thickness 600a becomes sufficiently small, the transition(s) between first major surface 230c and second major surface 230d can form a single (effective) cutting edge 270e, 270f on one or both of side edges 260c, 260d. In other words, the junction between first major surface 230c and side edge 260c may not be surgically distinguishable over the junction between second major surface 230d and side edge 260c in some embodiments. Thus, side edge 260c, in effect, becomes or constitutes cutting edge 270e. The same can apply to side edge 260d, in which side edge 260d can become or constitute cutting edge 270f.

In one or more embodiments, body 200b can comprise at least one side edge 260c, 260d having a thickness less than or equal to about 0.01 inches, and a cross-sectional area 700b-to-number of longitudinal cutting edges ratio that is less than or equal to about 0.000150 in$^2$/E. In at least one embodiment, body 200b can have a cross-sectional height 800 greater than about 0.01 and/or at least one tapered portion 280. Thus, in at least one embodiment, body 200b can comprise a rounded and/or lenticular cross-section (or cross-sectional shape or configuration) as illustrated in FIG. 4A.

Furthermore, with a side edge thickness 600a less than or equal to about 0.01 inches, side edge 260c can produce and/or present (only) one (effective) longitudinal cutting edge 270e in certain embodiments. Similarly, side edge 260d, having a thickness 600a less than or equal to about 0.01 inches, can also produce and/or present (only) one (effective) longitudinal cutting edge 270f in certain embodiments. Thus, a body 200b having sided edges 260c and 260d with side edge thicknesses 600a less than or equal to about 0.01 inches can comprise only two effective cutting edges 270e, 270f (e.g., as opposed to four effective cutting edges 270a, 270b, 270c, and 270d as in body 200 and/or 200a).

Those skilled in the art will also appreciate that a variety of cross-sectional shapes and/or configurations can be implemented in certain embodiments of the present disclosure. Various cross-sectional configurations can include straight, linear, curved, rounded, jagged, angled, and/or other edges, surfaces, and/or other components. For instance, certain embodiments can include one or more tapered portions having a rounded or curved form or configuration. Other embodiments can include one or more straight or linear tapered portions. Combinations of rounded or curved and straight or linear tapered portions are also contemplated herein. Likewise, a variety of side edges are contemplated herein, including broad, narrow, rounded, pointed, sharpened, and/or other shapes, forms, and/or configurations. Combinations of various side edges are also contemplated herein.

FIGS. 5A-5H, for instance, illustrate some variations on the embodiments illustrated in the foregoing figures. FIG. 5A illustrates a body 200c having a side edge 260a, a substantially straight or linear tapered portion 280c, and a side edge 260c. Accordingly, body 200c can have three effective cutting edges 270a, 270b, and 270e in some embodiments. FIG. 5B illustrates a body 200d having a substantially curved or rounded tapered portion 280f. FIG. 5C illustrates a body 200e having a substantially straight or linear first major surface 230a and a substantially curved or rounded second major surface 230c. Accordingly, body 200e (or second major surface 230c thereof) can include two tapered portions 280h. FIG. 5D illustrates a body 200f having two substantially straight or linear tapered portions 280e.

In some embodiments, one or more major surfaces, side edges, and/or effective cutting edges can have an extended configuration. For instance, FIG. 5E illustrates a body 200g having an extended or protruding side edge 260e. Furthermore, body 200g includes two inverted tapered portions 280g adjacent to extended or protruding side edge 260e and two substantially straight or linear tapered portions 280e extending from inverted tapered portions 280g. FIG. 5F illustrates a body 200h having four major surfaces 230e, 230f, 230g, and 230h. Major surfaces 230e and 230f, as well as major surfaces 230g and 230h are separated by (or merge or transition into) side edges 260a. Major surfaces 230e and 230g, as well as major surfaces 230f and 230h are separated by (or merge or transition into) side edges 260c. FIG. 5G illustrates a body 200i having four major surfaces 230i with intervening side edges 260c. FIG. 5H illustrates a body 200j having extended or protruding side edges 260e.

Those skilled in the art will appreciate that sizes, shapes, configurations, transitions, and/or radii of curvatures can be modified based on the requirements of the surgeon or other user. For instance, an exemplary body illustrating side edge(s) 260c, for instance, can alternatively be configured with side edge(s) 260a, 260e, and/or any other side edge(s) disclosed and/or described herein. Exemplary illustration of a particular side edge is not necessarily limited to the illustrated side edge. Rather, any suitable combination of side edge(s), cutting edge(s), major surface(s), etc. is contemplated herein. Thus, side edge(s) appearing to correspond to a measurement of less than or equal to 0.01 inches are not so limited. Instead, such side edge(s) can alternatively comprise measurement(s) greater than 0.01 inches without necessarily departing from the scope of this disclosure.

Figure 6A:
FIGS. 6A-6E each illustrate a cross-sectional view of an exemplary electrosurgical electrode according to an embodiment of the present disclosure.
Figure 6B:
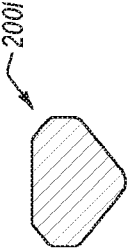
Figure 6C:
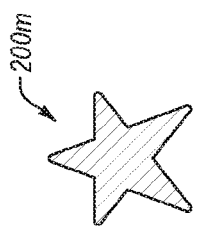
Figure 6D:
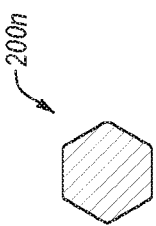

FIGS. 6A-6E illustrate a variety of geometric cross-sectional shapes and/or configurations. For instance, FIG. 6A illustrates a body 200k having a substantially square cross-sectional configuration. Those skilled in the art will appreciate, however, that a wide variety of quadrilateral configurations can be implemented in various embodiments of the present disclosure. For instance, body 200k can also or alternatively comprise a rectangular, rhomboidal, trapezoidal, cross-sectional configuration. Parallelograms are also contemplated herein.

Figure 6E:
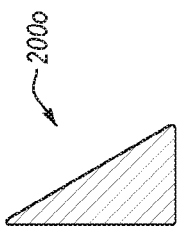

Other polygonal configurations (including concave, convex, regular, and irregular) are also contemplated herein, including a body 200l having a diamond-shaped cross section (FIG. 6B), a body 200m having a star-shaped cross section (FIG. 6C), a body 200n having a hexagonal-shaped cross section (FIG. 6D), and a body 200o having a triangular-shaped cross section FIG. 6E). One will also appreciate that pentagons, heptagons, octagons, and other polygonal configurations are also contemplated herein. Moreover, a triangular-shaped configuration can comprise an equilateral triangle, an isosceles triangle, a scalene triangle, a right triangle, an acute triangle, and/or an obtuse triangle.

Figure 7A:
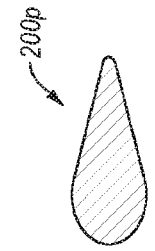
FIGS. 7A-7O each illustrate a cross-sectional view of an exemplary electrosurgical electrode according to an embodiment of the present disclosure.
Figure 7B:
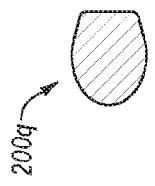
Figure 7C:
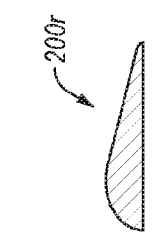
Figure 7D:
Figure 7E:
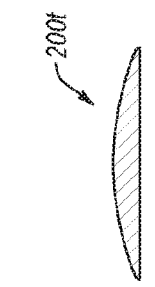
Figure 7F:
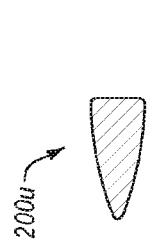

Some embodiments can include various non-geometric, rounded, partially-rounded, or other shapes, forms, and/or configurations. For instance, FIG. 7A illustrates a body 200p having an airfoil or tear-drop cross-section or cross-sectional configuration. FIG. 7B illustrates a body 200q having a partial (e.g., half) airfoil or tear-drop cross-section. FIG. 7C likewise illustrates a body 200r having a partial (e.g., half) airfoil or tear-drop cross-section. FIG. 7D illustrates a body 200s having a lenticular cross-section. FIG. 7E illustrates a body 200t having a partial (e.g., half) lenticular cross-section. FIG. 7F likewise illustrates a body 200u having a partial (e.g., half) lenticular cross-section. One will appreciate, however, that "partial" as used herein can also include a quarter, three-quarter, or other portion of a complete shape or configuration.

Figure 7G:
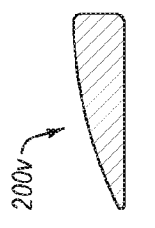
Figure 7H:
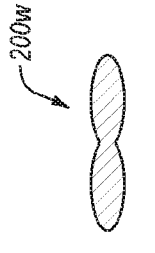
Figure 7I:
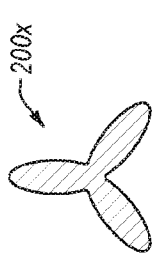
Figure 7J:
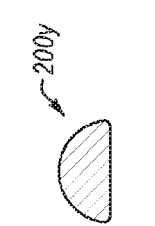
Figure 7K:
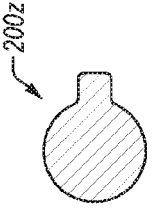
Figure 7L:
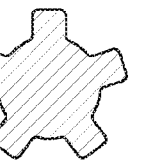
Figure 7M:
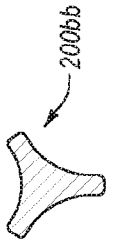
Figure 7N:
Figure 7O:
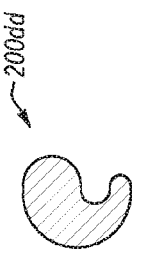

FIG. 7G illustrates a body 200v having a partial (e.g., half) cone cross-section. Full cone and other similar configurations are also contemplated herein. FIG. 7H illustrates a body 200w having a bi-lobe cross-section. FIG. 7I illustrates a body 200x having a tri-lobe cross-section. One will appreciate that other multi-lobe configurations are also contemplated herein. FIG. 7J illustrates a body 200y having a semi-circular cross-section. FIG. 7K illustrates a body 200z having a round cross-section with one abutment. FIG. 7L illustrates a body 200aa having a round cross-section with a plurality of abutments. FIG. 7M illustrates a body 200bb having a ninja star cross-section. FIG. 7N illustrates a body 200cc having an arrowhead cross-section. FIG. 7O illustrates a body 200dd having a partial "yin-yang" cross-section (e.g., half yin-yang, etc.).

Various cross-sectional configurations can also adopt such shapes as Arabic, Roman, or other letters or written characters. For instance, FIG. 8A illustrates a body 200ee having a "C"-shaped cross-section. FIG. 8B illustrates a body 200ff having a "D"-shaped cross-section. FIG. 8C illustrates a body 200gg having an "L"-shaped cross-section. FIG. 8D illustrates a body 200hh having a "J"-shaped cross-section. FIG. 8E illustrates a body 200ii having a "T"-shaped cross-section. FIG. 8F illustrates a body 200jj having an "X"-shaped cross-section. FIG. 8G illustrates a body 200kk having a "V"-shaped cross-section.

The cross-sectional configuration of one or more embodiments of the present disclosure can be uniform from the first end of the body to the second end of the body. Those skilled in the art will appreciate, however, that variable cross-sectional configurations are also contemplated herein. For instance, the tip of the body can be tapered in one or more embodiments, giving the body a variable cross-sectional configuration between the first end and the second end thereof. Furthermore, cross-sectional configuration can change along the length of the body without departing from the scope of this disclosure. Similarly, the length of the elongated body between the first end and the second end need not be perfectly or substantially planar and/or linear. For instance, curves, bends, and/or other changes in elongated shape are also contemplated herein.

The working ends of electrosurgical electrodes can be configured to provide great versatility in cutting and/or cauterizing tissue and/or blood vessels in a variety of different surgical procedures. Furthermore, the electrode tips can be configured to produce significantly improved performance in cutting efficiency, dramatic reduction in unwanted tissue damage, and improved post-operative recovery. For instance, each of the electrodes illustrated in the foregoing figures can include or be formed with one or more shaped or sharpened working edges. The shaped working edges can further concentrate the electrical energy transferred from the electrode to the patient's tissue. The further concentrated electrical energy can further reduce the amount of extraneous charge loss into surrounding tissue by increasing the incision speed, thereby reducing the activation time and level of thermal necrosis in tissues surrounding the incision site.

Similarly, each of the illustrated electrodes can be formed with a limited thickness, height, width, and/or mass to limit the amount of latent heat or thermal energy that can build up in the electrode. Reducing the amount of latent heat within the electrode can further reduce the amount of latent heat that is transferred from the electrode to the tissue, which reduces the amount of tissue damage caused in tissue surrounding the incision site.

Additionally, a non-stick coating can serve to eliminate or reduce the clinging of charred tissue to the blade, thereby reducing incidences of unwanted tissue damage. A non-stick material suitable for use as a coating can be, but is not limited to, PTFE or a hybrid material that can include a combination of at least one of an organic material and an inorganic material, and that provides the coated surface with desirable properties, such as a high temperature stability, flexibility, and a low temperature application condition so that the coating layer may be applied by a spray or dip process. An example of a hybrid coating is provided in U.S. Pat. No. 6,951,559, entitled "Utilization of a Hybrid Material in a Surface Coating of an Electrosurgical Instrument" that issued on Oct. 4, 2005 to Greep, the disclosure of which is incorporated herein by reference in its entirety.

The foregoing examples and embodiments represent exemplary embodiments and are provided for illustrative purposes only. Accordingly, the disclosed examples and embodiments are meant to illustrate one or more aspects of the invention and are not intended to limit the scope of the present invention. A variety of aspects compatible with and/or contemplated within the scope of one or more embodiments of the present disclosure can be found in U.S. Pat. Nos. 5,496,315, 5,697,926, 5,893,849, 6,039,735, 6,039,735, 6,066,137, 8,439,910, and 8,500,727, the entirety of each of which is incorporated herein by reference.

It is to be understood that this disclosure is not limited to parameters of the particularly exemplified products, processes, compositions, kits, and/or methods, which may, of course, vary. It is also to be understood that the terminology used herein is only for the purpose of describing particular embodiments of the present disclosure, and is not intended to limit the scope of the invention in any manner.

Additionally, the terms "including," "having," "involving," "containing," "characterized by," and variants thereof (e.g., "includes," "has," and "involves," "contains," etc.) as used herein, including in the claims, shall be inclusive and/or open ended, shall have the same meaning as the word "comprising" and variants thereof (e.g., "comprise" and "comprises"), and does not exclude additional, un-recited elements or method steps, illustratively.

It will be noted that, as used in this specification and the appended claims, the singular forms "a," "an" and "the" include plural referents unless the content clearly dictates otherwise. Thus, for example, reference to a "side edge" includes one, two, or more support members.

Various aspects of the present disclosure may be illustrated with reference to one or more exemplary embodiments. As used herein, the term "exemplary" means "serving as an example, instance, or illustration," and should not necessarily be construed as preferred or advantageous over other embodiments disclosed herein.

It will also be appreciated that where a range a values (e.g., less than, greater than, at least, or up to a certain value, or between two recited values) is disclosed or recited in connection with any of the embodiments described herein, any specific value or range of values falling within the disclosed range of values is likewise disclosed and contemplated herein. For instance, disclosure of a cross-sectional area-to-longitudinal cutting edges ratio less than or equal to 0.0004 in$^2$/E, or between 0 and 0.0004 in$^2$/E, includes, illustratively, a specific disclosure of: (i) a cross-sectional area-to-number of longitudinal cutting edges ratio of 0.0001 in$^2$/E, 0.00025 in$^2$/E, 0.000399 in$^2$/E, 0.0004 in$^2$/E, or any other value between 0 and 0.0004 in$^2$/E; and/or (ii) a cross-sectional area-to-number of longitudinal cutting edges ratio between 0.00001 in$^2$/E and 0.00035 in$^2$/E, between 0.0002 in$^2$/E and 0.0003 in$^2$/E, between 0.00025 in$^2$/E and 0.000275 in$^2$/E, and/or any other range of values between 0 and 0.0004 in$^2$/E.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only preferred materials and methods are described herein.

While various aspects and embodiments have been disclosed herein, other aspects and embodiments are contemplated. The various aspects and embodiments disclosed herein are for purposes of illustration and are not intended to be limiting. It is noted that products, processes, compositions, kits, and methods according to certain embodiments of the present invention may include, incorporate, or otherwise comprise properties, features, components, members, and/or elements described in other embodiments described and/or disclosed herein. Thus, reference to a specific feature in relation to one embodiment should not be construed as being limited to applications only within said embodiment. In addition, various embodiments can be combined to form additional embodiments without departing from the scope of the invention or this disclosure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the products, processes, compositions, kits, and methods disclosed herein may be made without departing from the scope of the invention, which is defined in the appended claims. All changes which come within the meaning and range of equivalency of the claims are to be embraced within their scope. Various modifications that fall within the scope of the appended claims will be apparent to one skilled in the art.

What is claimed is:

1. An electrosurgical electrode adapted for use in performing electrosurgical operative procedures on patient tissue, the electrosurgical electrode comprising:

an elongated body extending longitudinally between a first end and a second end, the elongated body being formed of a conductive material and adapted to be electrically connected to an electrosurgical generator to facilitate communication of high frequency electrical energy from the electrosurgical generator to the electrosurgical electrode for communicating the radio-frequency electrical energy to the patient tissue for performing the electrosurgical operative procedures thereupon, wherein the elongate body comprises:

a first major surface and an opposing second major surface, the first and second major surfaces extending between the first end and the second end, each of the first and second major surfaces being exposed or uncovered by any other electrically conductive material of the electrosurgical electrode;

one or more longitudinal side edges extending between the first end and the second end and the first and second major surfaces, at least one of the one or more longitudinal side edges have a thickness less than or equal to 0.01 inches, the at least one of the one or more longitudinal side edges comprising only one longitudinal cutting edge;

a cross-sectional area that extends between and is defined by the first and second major surfaces and the one or more longitudinal side edges of the conductive material; and a cross-sectional area-to-number of longitudinal cutting edges ratio that is less than or equal to 0.000150 square inches per longitudinal cutting edge.

2. The electrosurgical electrode of claim 1, wherein the cross-sectional area has a cross-sectional height between the first major surface and the second major surface, the cross-sectional height being greater than 0.01 inches, at least one of the first major surface and the second major surface comprising one or more tapered portions extending from a portion of the at least one of the first major surface and the second major surface to the at least one of the one or more longitudinal side edges such that the thickness of the at least one of the one or more longitudinal side edges is less than or equal to 0.01 inches.

3. The electrosurgical electrode of claim 2, wherein the one or more longitudinal side edges comprises a plurality of longitudinal side edges disposed between the first major surface and the second major surface and extending at least one length between the first end of the elongated body and the second end of the elongated body, the one or more tapered portions comprising a plurality of tapered portions selected from the group consisting of:

a plurality of tapered portions extending from a portion of the first major surface to respective longitudinal side edges of the plurality of longitudinal side edges;

one or more tapered portions extending from a portion of the first major surface to one or more of the plurality of longitudinal side edges and one or more tapered portions extending from a portion of the second major surface to one or more of the plurality of longitudinal side edges;

a plurality of tapered portions extending from a portion of the first major surface to respective longitudinal side edges of the plurality of longitudinal side edges and one or more tapered portions extending from a portion of the second major surface to one or more of the plurality of longitudinal side edges; and a plurality of tapered portions extending from a portion of the first major surface to respective longitudinal side edges of the plurality of longitudinal side edges and a plurality of tapered portions extending from a portion of the second major surface to respective longitudinal side edges of the plurality of longitudinal side edges.

4. The electrosurgical electrode of claim 1, wherein the at least one of the one or more longitudinal side edges is continuous with the first major surface and the second major surface such that the longitudinal cutting edge thereof comprises a junction between the first major surface and the at least one of the one or more longitudinal side edges or between the second major surface and the at least one of the one or more longitudinal side edges.

5. The electrosurgical electrode of claim 1, further comprising a tip disposed at the first end of the elongated body.

6. The electrosurgical electrode of claim 5, wherein the tip is continuous with one or more of the first major surface, the second major surface, and the one or more longitudinal side edges, the tip comprising a configuration selected from the group consisting of a blunt configuration, a pointed configuration, a rounded configuration, and an angled configuration.

7. The electrosurgical electrode of claim 1, wherein the electrosurgical electrode is adapted for use in performing the electrosurgical operative procedures at a power level that is reduced by 10% or more compared to an electrosurgical blade electrode having a cross-section area-to-cutting edge ratio greater than about 0.000150 in$^2$/E.

8. The electrosurgical electrode of claim 1, further comprising an insulating coating covering at least a portion of the body.

9. The electrosurgical electrode of claim 8, wherein the insulating coating comprises a material selected from the group consisting of PTFE, silicone, ceramic, glass, chlorinated hydrocarbon, fluorinated hydrocarbon, diamond, a high temperature polymer, a hydrophilic polymer, and a capacitor dielectric, the insulating coating provided with a thickness that ensures transmission of the radio frequency electrical energy from the body to the tissue.

10. The electrosurgical electrode of claim 1, wherein the cross-sectional area comprises a cross-sectional shape or configuration selected from the group consisting of a star cross-section, a square cross-section, a rectangular cross-section, a rhomboidal cross-section, a trapezoidal cross-section, a parallelogram cross-section, a diamond cross-section, an airfoil or tear-drop cross-section, a partial airfoil or tear-drop cross-section, a triangular cross-section, a round cross-section with one or more abutments, a multi-sided cross-section, an arrowhead cross-section, a "C" cross-section, a "D" cross-section, an "L" cross-section, a "J" cross-section, a "T" cross-section, an "X" cross-section, a lenticular cross-section, a partial lenticular cross-section, a multi-lobe cross-section, and a semi-circular cross-section.

11. The electrosurgical electrode of claim 1, wherein the cross-sectional area has a cross-sectional width less than or equal to 0.055 inches.

12. The electrosurgical electrode of claim 1, wherein the electrosurgical electrode is configured such that:
the elongated body comprises one or more concave portions and the cross-sectional area comprises an area circumscribed by the elongated body and the one or more concave portions; or
the elongated body comprises a convex body and the cross-sectional area comprises the area occupied by the elongated body.

13. An electrosurgical electrode adapted for use in performing an electrosurgical operative procedure on patient tissue, the electrosurgical electrode comprising:
an elongated body extending longitudinally between a first end and a second end, the elongated body being formed of a conductive material and adapted to be electrically connected to an electrosurgical generator to facilitate communication of radio frequency electrical energy from the electrosurgical generator to the electrosurgical electrode for communicating the radiofrequency electrical energy to the patient tissue for the performing of electrosurgical operative procedures thereupon, the elongated body having:
first and second opposing major surfaces extending between the first end and the second end, each of the first and second opposing major surfaces being exposed or uncovered by any other electrically conductive material of the electrosurgical electrode;
first and second longitudinal side edges extending from the first end towards the second end and each having a thickness; and
a cross-sectional area defined by the first and second opposing major surfaces and the first and second longitudinal side edges,
wherein
the thickness of the first longitudinal side edge is greater than 0.01 inches, the first longitudinal side edge having two or more longitudinal cutting edges, each of the two or more longitudinal cutting edges being formed by a junction between one of the first and second opposing major surfaces and the first longitudinal side edge,
the thickness of the second longitudinal side edge being less than or equal to 0.01 inches, the second longitudinal side edge comprising only a single longitudinal cutting edge, the single longitudinal cutting edge being configured to concentrate the radiofrequency electrical energy along the single longitudinal cutting edge, and
a cross-sectional area-to-number of longitudinal cutting edges ratio that is less than or equal to 0.001 square inches per longitudinal cutting edge.

14. The electrosurgical electrode of claim 13, wherein the electrosurgical electrode is configured such that:
the elongated body comprises one or more concave portions and the cross-sectional area comprises an area circumscribed by the elongated body and the one or more concave portions; or
the elongated body comprises a convex body and the cross-sectional area comprises the area occupied by the elongated body.

15. The electrosurgical electrode of claim 13, wherein the first and second longitudinal side edges are disposed between the first major surface and the second major surface.

16. The electrosurgical electrode of claim 15, wherein at least one of the first and second longitudinal side edges is continuous with the first major surface and the second major surface such that:
at least one of the two or more longitudinal cutting edges comprises a junction between the first major surface and the at least one of the first and second longitudinal side edges; and
at least one of the two or more longitudinal cutting edges comprises a junction between the second major surface and the at least one of the first and second longitudinal side edges.

17. The electrosurgical electrode of claim 16, further comprising a tip disposed at the first end of the elongated body.

18. The electrosurgical electrode of claim 17, wherein the tip is continuous with one or more of the first major surface, the second major surface, and the first and second longitudinal side edges, the tip comprising a configuration selected from the group consisting of a blunt configuration, a pointed configuration, a rounded configuration, and an angled configuration.

19. The electrosurgical electrode of claim 13, further comprising one or more additional longitudinal side edges.

20. The electrosurgical electrode of claim 13, wherein the cross-sectional area has a cross-sectional width between the first and second longitudinal side edges less than or equal to 0.055 inches.

21. The electrosurgical electrode of claim 13, wherein the cross-sectional area comprises a cross-sectional shape or configuration selected from the group consisting of a star cross-section, a partially square cross-section, a partially rectangular cross-section, a rhomboidal cross-section, a trapezoidal cross-section, a parallelogram cross-section, a diamond cross-section, an airfoil or tear-drop cross-section, a partial airfoil or tear-drop cross-section, a triangular cross-section, a round cross-section with one or more abutments, a multi-sided cross-section, an arrowhead cross-section, a "C" cross-section, a "D" cross-section, an "L" cross-section, a "J" cross-section, a "T" cross-section, an "X" cross-section, a lenticular cross-section, a partial lenticular cross-section, a multi-lobe cross-section, and a semi-circular cross-section.

22. The electrosurgical electrode of claim 13, further comprising an insulating coating covering at least a portion of the elongated body.

23. The electrosurgical electrode of claim 22, wherein the insulating coating comprises a material selected from the group consisting of PTFE, silicone, ceramic, glass, fluorinated hydrocarbon, diamond, a high temperature polymer, a hydrophilic polymer, and a capacitor dielectric, and is provided with a thickness that ensures transmission of the radio frequency electrical energy from the elongated body to the tissue.

24. The electrosurgical electrode of claim 13, wherein the electrosurgical electrode is adapted for use in performing the electrosurgical operative procedures at a power level that is reduced by 10% or more compared to an electrosurgical blade electrode having a cross-section area-to-cutting edge ratio greater than about 0.001 $in^2/E$.

* * * * *